United States Patent [19]

Sarstedt

[11] 4,449,539
[45] May 22, 1984

[54] BLOOD EXTRACTION DEVICE

[75] Inventor: Walter Sarstedt, Nümbrecht, Fed. Rep. of Germany

[73] Assignee: Walter Sarstedt Kunstoff-Spritzgusswerk, Fed. Rep. of Germany

[21] Appl. No.: 335,902

[22] Filed: Dec. 30, 1981

[30] Foreign Application Priority Data

Dec. 30, 1980 [DE] Fed. Rep. of Germany ....... 3049503

[51] Int. Cl.³ .............................................. A61B 5/00
[52] U.S. Cl. ..................................... 128/764; 128/765
[58] Field of Search ............... 128/763, 764, 765, 766, 128/218 N; 604/86, 87, 88, 89

[56] References Cited

U.S. PATENT DOCUMENTS

| | | | |
|---|---|---|---|
| 1,793,068 | 2/1931 | Dickinson | 128/218 N |
| 2,371,086 | 3/1945 | Watson et al. | 128/216 |
| 2,671,449 | 3/1954 | Dann | 128/218 N |
| 2,711,171 | 6/1955 | Dunnican | 128/218 N |
| 2,828,742 | 4/1958 | Ashkenaz | 128/218 |
| 3,096,763 | 7/1963 | McConnaughey | 128/221 |
| 3,366,103 | 1/1968 | Keller | 128/764 |
| 3,382,865 | 5/1968 | Worrall, Jr. | 128/764 |
| 3,395,696 | 8/1968 | Brown et al. | 128/764 |
| 3,503,386 | 3/1970 | Pieratt | 128/764 |
| 3,536,061 | 10/1970 | Ogle | 128/764 |
| 3,585,984 | 6/1971 | Buchanan | 128/764 |
| 3,848,593 | 11/1974 | Baldwin | 128/218 N |
| 3,931,815 | 1/1976 | Takatsuki | 128/764 |
| 3,994,295 | 11/1976 | Wulff | 128/218 N |
| 4,027,669 | 6/1977 | Johnston et al. | 128/218 N |
| 4,220,151 | 9/1980 | Whitney | 128/218 N |
| 4,221,218 | 9/1980 | Pfleger | 128/218 D |
| 4,240,424 | 12/1980 | Akhavi | 128/218 N |
| 4,256,120 | 3/1981 | Finley | 128/763 |

FOREIGN PATENT DOCUMENTS

| | | | |
|---|---|---|---|
| 188846 | 4/1956 | Fed. Rep. of Germany | 128/218 N |
| 1812742 | 7/1969 | Fed. Rep. of Germany | 128/764 |
| 1593629 | 7/1970 | France | 128/218 N |
| 880516 | 11/1970 | Italy | 128/764 |
| 1036000 | 7/1966 | United Kingdom | . |

Primary Examiner—Richard J. Apley
Assistant Examiner—Harry J. Macey
Attorney, Agent, or Firm—Townsend & Townsend

[57] ABSTRACT

A blood extraction device is disclosed herein, which is an improvement over similar devices having a cylindrical extraction tube enclosing an air-tight piston and sealed with a closure cap having an axial projection which contains a self-sealing puncturable plug and is received within a movable tubular guide sleeve containing a double-ended cannula the rear end of which is enclosed by a deformable but resilient thin hose with a closed self-sealing rear end. The improvement resides in the inclusion of one or more slots on the guide sleeve and cooperating lugs on the projection, or vice versa, each slot having an axially extending portion and a peripherally extending portion, such that rotation of the rear cutting edge of the cannula is prevented during penetration of both the rear end of the hose and the plug, and rotation is possible only when penetration is complete. In this way, the self-sealing properties of both the hose and the plug are retained, and the resilience of the hose secures each lug in position in the peripherally extending portion of each slot.

6 Claims, 7 Drawing Figures

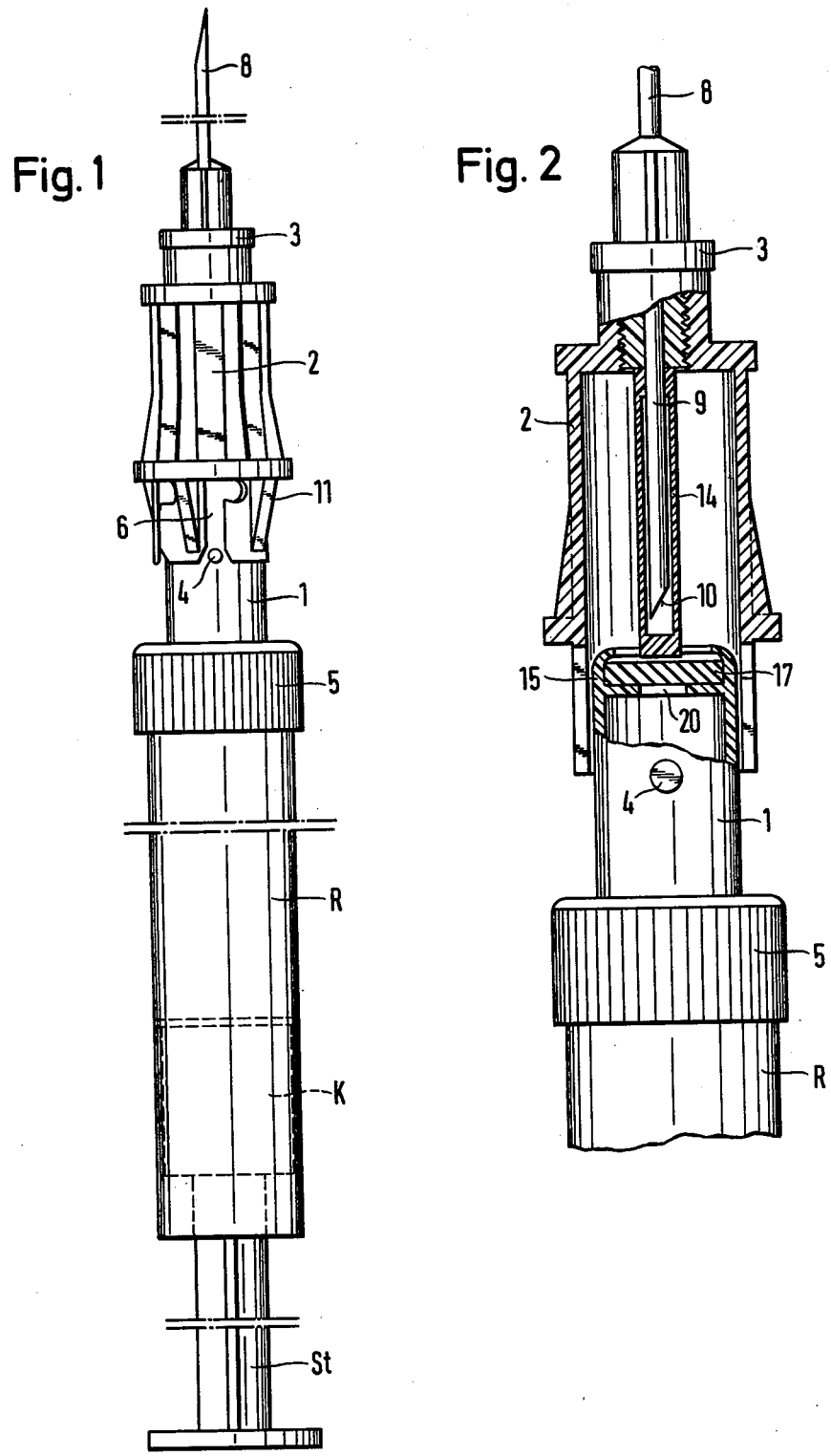

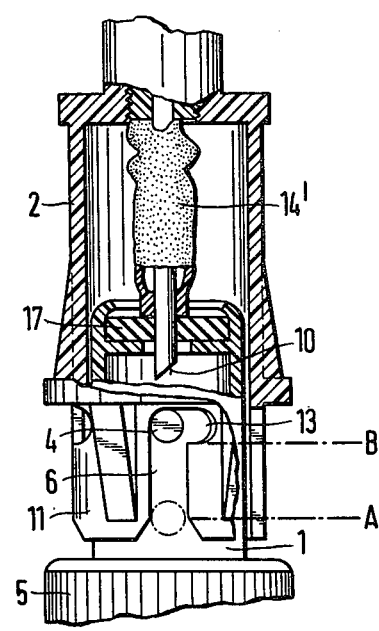
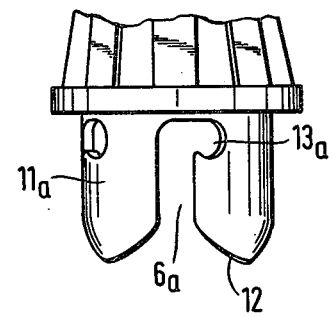
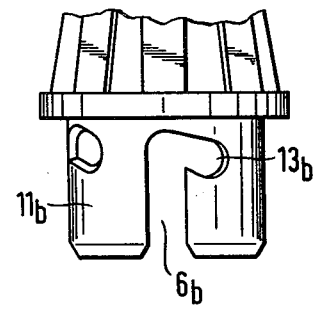

BLOOD EXTRACTION DEVICE

BACKGROUND OF THE INVENTION

1. Field of the Invention

A blood extraction device is known from U.S. Pat. No. 3,931,815 having a cylindrial extraction tube, a piston movable in an air-tight manner within said tube, a closure cap carrying a projection at the front end of the tube and a tubular guide sleeve which can be pushed onto the extraction tube. The guide sleeve carries at its front end a double-ended cannula having front and rear ends provided with respective cutting edges.

A closure plug puncturable by the cannula is arranged in the projection and the plug is made of a material which is self-sealing on removal of the cannula. The front end of the cannula which projects from the guide sleeve is provided for insertion into a vein whereas the rear end of the cannula is sealingly covered by a thin hose and projects sufficiently far into the guide sleeve that, on pushing the guide sleeve onto the extraction tube, the rear end of the cannula first of all punctures a rear end of the hose and then punctures the closure plug.

Axial guide means are provided between the guide sleeve and the extraction tube and are operative as the rear cutting edge of the cannula penetrates the closed rear end of the hose and then over at least a part of the movement of the rear cutting edge of the cannular through the material of the closure plug. In this arrangement the axial guide means takes the form of an axial tongue and groove guide provided between the extraction tube and the guide sleeve. The function of this axial guide means is to prevent relative rotation between the extraction tube and the guide sleeve when the actuating rod for the piston is screwed onto the piston. If the guide sleeve is pushed over the extraction tube the rear cutting edge of the cannula first of all cuts through the base of the rubber hose surrounding the rear end of the cannula and then through the closure plug at the front end of the projection on the closure cap of the extraction tube. Following this movement an annular rib provided on the inner wall of the guide sleeve snaps into a peripheral groove of the extraction tube so that further relative displacement between the guide sleeve and the extraction tube is avoided to a certain degree. This snap connection does not however adequately ensure that the required relative axial position between the guide sleeve and the extraction tube is retained during subsequent actuation of the piston arranged in the extraction tube.

It is also known (from German patent application No. P 18 12 742) to screw the guide sleeve onto an external thread provided on the projection of the extraction tube. This arrangement has, however, the disadvantage that the rear cutting edge of the cannula rotates as it passes through the base of the rubber hose and the closure plug. This can cause the rubber hose and the plug to wind up as they are penetrated which leads to a deterioration of the self-sealing characteristics of the penetrated parts on removal of the end of the cannula.

The principal object underlying the present invention is to provide a blood extraction device in which the guide sleeve can be easily slid onto the projection without disadvantageously affecting the self-sealing action of the punctured parts on removal of the cannula, and in which the axial position of the guide sleeve relative to the projection can be secured after it has been pushed onto the projection in such a way that a reliable connection is ensured between these components, even when strong axial forces act on the extraction tube.

SUMMARY OF THE INVENTION

In order to satisfy this object there is provided, in accordance with the present invention, a blood extraction device having a cylindrical extraction tube, a piston movable in an air-tight manner within said tube, a closure cap carrying a projection at the front end of said tube, a tubular guide sleeve which can be pushed onto said extraction tube and which carries at its front end a cannula having front and rear ends provided with respective cutting edges, a closure plug puncturable by the cannula arranged in said projection, with said plug being self-sealing on removal of said cannula, wherein the front end of the cannula which projects from the guide sleeve is provided for insertion into a vein whereas the rear end of the cannula is sealingly covered by a thin hose and projects sufficiently far into the guide sleeve that, on pushing the guide sleeve onto the extraction tube, the rear end of the cannula first of all punctures a rear end of the hose and then punctures the closure plug, and wherein axial guide means are provided between the guide sleeve and the extraction tube and are operative as the rear cutting edge of the cannula penetrates the closed rear end of the hose and over at least a part of the movement of the rear cutting edge of the cannula through the material of the closure plug, characterised in that a twist actuated locking mechanism actuatable only after substantial or complete puncturing of the closure plug is provided between the guide sleeve which is pushed onto the projection of the closure cap and the projection.

2. Description of the Prior Art

Thus, in accordance with the invention, the use of a latch-like snap connection to axially secure the guide sleeve to the extraction tube is dispensed with so that a slack fit is possible between the projection and the guide sleeve which allows the guide sleeve to be easily pushed in an axial direction onto the projection. The axial location is then effected by a twist actuated locking mechanism and indeed in such a way that relative rotation or twisting between the guide sleeve and the projection can only take place when the closure plug has been at least extensively penetrated by the rear cutting edge of the cannula.

Thus relative rotation only takes place between the smooth outerwall parts of the cannula and the penetrated region of the base of the rubber hose and the closure plug. This prevents wind up and possible tearing of these components and does not lead to a reduction of their self-sealing properties.

At the same time an axial connection is provided between the guide sleeve and the extraction tube which cannot be released by axial forces but which can however be easily released by rotation of the twist actuated locking mechanism in the opposite direction.

It is indeed known from U.S. Pat. No. 3,503,386, in connection with a spring force actuated device for withdrawing the rear end of a cannula from the closure plug of an extraction tube, to provide a bayonet closure between the two abutments of the spring. The longitudinal guide provided by this bayonet closure does not however prevent relative rotation between the guide sleeve and the closure plug during penetration of the closure plug by the end of the cannula. Accordingly the danger of wind up of the closure plug is ever present. Furthermore, the bayonet connection does not allow the extraction tube and the guide sleeve to be axially fixed to one another.

The advantages offered by the present invention, and in particular the avoidance of a snap-like connection between the guide sleeve and the extraction tube, will be apparent if one considers the manner in which a blood extraction device is used to draw blood from a patient's vein.

The usual method of extracting blood from a patient is for the operator or doctor to insert the front end of the cannula into the vein and then to push the extraction tube relative to the guide sleeve so that the rear end of the cannula penetrates the rubber hose and the closure plug. Clearly the jolt which would occur in the prior art device as the snap connection engages is most unsatisfactory. It can readily cause the front end of the cannula to penetrate both walls of the vein with accompanying discomfort to the patient. The situation becomes worse as the snap connection is made stronger in an attempt to ensure an adequate axial connection between the guide sleeve and the extraction tube.

In contrast the twist actuated locking mechanism of the present invention can be operated with a minimum of force so that no jolt results as the locking mechanism engages. Furthermore, as pointed out above, the locking mechanism of the present invention can only be engaged after the cannula has penetrated the closure plug so that wind up of the closure plug is prevented. It will be appreciated that the use of the twist actuated locking mechanism proposed herein provides a very adequate axial connection between the guide sleeve and the extraction tube which is of benefit to the doctor or operator as he slowly withdraws the piston to suck blood from the patient's vein through the cannula into the extraction tube.

If necessary the twist actuated locking mechanism between the guide sleeve and the extraction tube can be released with the cannula still present in the patient's vein so that a second sample can be taken using a further extraction tube, without the need to reinsert a fresh cannula into the patient and without the act of separating the guide sleeve and the first extraction tube giving rise to a sudden jolt or other disadvantageous effect.

Further advantageous embodiments of the invention are characterised in the accompanying subclaims.

The invention will now be described by way of example only and with reference to the accompanying drawings which show:

BRIEF DESCRIPTION OF THE DRAWINGS

FIG. 1 a partly interrupted side view of a blood extraction device having an extraction tube and a guide sleeve carried by a projection on a closure cap at the front end of this extraction tube, FIG. 2 an enlarged partially sectioned side view of the front part of this device, FIG. 3 a partially sectioned side view similar to that of FIG. 2 but showing the condition in which the guide sleeve is pushed over the projection, FIG. 4 an enlarged partial side view of a further embodiment of the guide sleeve, FIG. 5 a side view similar to FIG. 4 as a further embodiment and FIGS. 6 and 7 two further embodiments of the guide sleeve.

Figure 6:
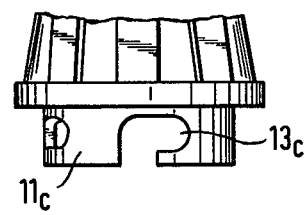

The blood extraction device shown in FIGS. 1 to 3 includes a cylindrical extraction tube R and a piston K with an attached piston rod St which is movable in an air-tight manner within the extraction tube. The tube R is closed at its front end by a closure cap 5 from which a cylindrical projection 1 of somewhat smaller diameter projects in the axial direction. The projection is closed at its front end by a puncturable closure plug 17 which sits on an end plate of the projection 1. The end plate has a central bore 20 and the closure plug is retained in position against this end plate by a collar 15 which is turned over around the outer edge of the closure plug.

A retaining lug 4 which is formed integrally with the wall of the projection 1 projects radially sideways from the projection 1.

A guide sleeve 2 is axially displaceably and rotatably arranged on the projection 1. A holder 3 with a cast in cannula 8 is screwed into the front narrowed end of the guide sleeve. The cannula is of the double-ended type and is sharpened, i.e. provided with cutting edges at its front and rear ends. The front end of the cannula is for introduction into a vein whereas the rear end 9 projects beyond the holder 3 into the guide sleeve 2. The rear end 9 of the cannula is shorter than the front end which is intended for introduction into the vein.

As seen in FIG. 2 a sack-like rubber hose 14 is pushed over the rear end 9 of the cannula and has a length such that the rear cutting edge 10 of the rear end 9 of the cannula does not touch the base or rear end of the elongate rubber hose 14.

In the rear region of the guide sleeve 2 (which can be provided with internal longitudinal ribs which facilitate the engagement of the guide sleeve over the projection 1 despite good guidance) there are provided axial slots 6 which are distributed around the periphery of the guide sleeve. The width of the slots is somewhat larger than the thickness of the retaining lug 4. At their front ends the axial slots merge into lateral enlargements or recesses 13 which effectively represent a continuation of the axial slots in the peripheral direction.

On placing the guide sleeve 2 on the projection 1 the retaining lug 4 is introduced into one of the axial slots around the periphery of the guide sleeve. As the guide sleeve is pushed further over the end of the projection the base of the rubber hose 14 contacts the closure plug 17 whereupon the cutting edge 10 of the rear end 9 of the cannula engages the closed end of the rubber hose 14. The retaining lug 4 has now entered completely into the axial slot 6 (chain dotted representation A in FIG. 3) and an axial guide is established between the guide sleeve 2 and the projection 1. The guide sleeve 2 is therefore guided relative to the projection 1 so that only axial movement is possible. From now on rotation of the guide sleeve 2, and thus of the cutting edge 10 of the cannula, relative to the projection 1 is no longer possible. Further downward movement (as seen in the drawing) of the guide sleeve 2 onto the projection 1 results in the cutting edge 10 firsly puncturing or penetrating the base of the rubber hose 14 and then puncturing or penetrating the closure plug 17.

As seen in FIG. 3 the length of the axial slots 6 and the arrangement of the retaining lug 4 are so chosen that the retaining lug 4 is guided in the axial slot 6 up to a position B at which the cutting edge 10 of the cannula 8 has already fully punctured the closure plug 17.

As soon as the parts have reached the position illustrated in FIG. 3 the guide sleeve 2 can be twisted or rotated relative to the projection 1 on the closure cap 5 so that the retaining lug 4 enters into the short angled enlargement, recess or cut-out 13 and axially locks the guide sleeve to the projection.

The cooperating retaining lug 4 and enlargement 13 thus form a twist actuated locking mechanism between the guide sleeve and the projection. Clearly more than one retaining lug can be provided if required.

As seen in FIG. 3 the rubber sleeve 14 is collapsed in concertina-like manner as the guide sleeve 2 is pushed over the projection 1 so that it reaches the form 14' illustrated in FIG. 3. As a result of its resilience the rubber hose now exerts an axial force which tries to push the projection 1 out of the guide sleeve 2. This is however prevented by the retaining lug 4 which has entered into the enlargement or recess 13. A twist actuated locking mechanism is thus present between the guide sleeve 2 and the projection 1 which can become effective only when the cutting edge 10 has punctured the base of the rubber hose 14 and the closure plug 17.

As seen in FIG. 4 the enlargement 13a can be made somewhat wider at its end so that the retaining lug, after entry into the enlargement 13a, is secured against unintentional reverse rotation because the axial force exerted by the rubber hose 14 in its concertina-like collapsed condition tries to push the guide sleeve 2 away from the projection 1 so that the retaining lug 4 is pressed into the broadened end of the enlargement and thus additionally secures the locking mechanism.

The rear region 11a of the guide sleeve 2 is provided in this embodiment with several axial slots 6a around its periphery and these slots have at their inlet ends funnel-like enlargements 12 which adjoin one another.

In the embodiment shown in FIG. 5 the rear region 11b of the guide sleeve 2 is once again provided with a plurality of axial slots 6b distributed around its periphery. The enlargement 13b at the end of each axial slot 6b is inclined rearwardly at an acute angle.

Figure 7:
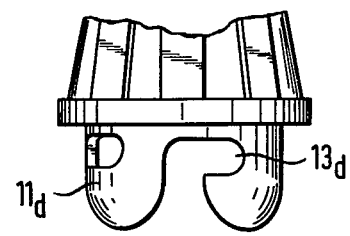

FIGS. 6 and 7 show embodiments with a short axial slot in the rear region 11c of the guide sleeve 2 which is then followed by the short angled enlargement 13c or 13d. The axial slot must however be sufficiently long to ensure axial guidance of the guide sleeve 2 relative to the projection as the cutting edge 10 punctures the base of the rubber hose 14 and at least a part of the closure plug 17. In the embodiment of FIG. 7 the short axial slot also has a funnel-like enlargement at its front end.

I claim:

1. In a blood extraction device comprising:
   a cylindrical extraction tube;
   a piston movable in an air-tight manner within said tube;
   a closure cap carrying a projection at the front end of said tube;
   a tubular guide sleeve which can be pushed over said projection and which carries a cannula having front and rear ends provided with respective cutting edges;
   a closure plug puncturable by the cannula arranged in said projection, with said plug being self-sealing on removal of said cannula, wherein said front end of said cannula projects out of said guide sleeve and is provided for insertion into a vein and wherein said rear end of said cannula is sealingly covered by a thin hose having a closed rear end and projects sufficiently far into said guide sleeve that, on pushing said guide sleeve onto said projection, said rear end of said cannula first punctures said closed rear end of said hose and then punctures said closure plug; and
   connecting means provided between said guide sleeve and said projection, said connecting means comprising a slot provided on one of said guide sleeve and said projection and a cooperating lug engageable with said slot on the other one of said guide sleeve and said projection;

the improvement wherein:
   said slot has (a) a first axially extending portion operative as the rear cutting edge of the cannula punctures said closed rear end of said hose and said closure plug to prevent relative rotation between said guide sleeve and said projection, and (b) a second peripherally extending portion permitting relative rotation between said guide sleeve and said projection to a locked position preventing relative axial movement therebetween, wherein the length of the axial slot and the arrangement of the retaining lug are so chosen that the retaining lug is guided in the axial slot up to a position at which the rear cutting edge of the cannula has already fully punctured the closure plug, and
   said thin hose is of resilient material and is adapted to generate an axially directed resilient force for retaining said guide sleeve in said locked position thereby preventing unintentional release of said guide sleeve from said projection.

2. A blood extraction device in accordance with claim 1 wherein a plurality of slots with axially and peripherally extending slot portions are provided in said guide sleeve.

3. A blood extraction device in accordance with claim 2 wherein only a single lug is provided on said projection.

4. A blood extraction device in accordance with claim 2 wherein said axially extending slot portions terminate at a rear end of said guide sleeve in funnel-shaped openings.

5. A blood extraction device in accordance with claim 1 wherein said peripherally extending slot portion is angled rearwardly at an acute angle to said axially extending portion.

6. A blood extraction device in accordance with claim 5 wherein said peripherally extending slot portion includes an enlarged end portion.

* * * * *

UNITED STATES PATENT AND TRADEMARK OFFICE
CERTIFICATE OF CORRECTION

PATENT NO. : 4,449,539

DATED : May 22, 1984

INVENTOR(S) : Walter Sarstedt

It is certified that error appears in the above-identified patent and that said Letters Patent is hereby corrected as shown below:

On the cover page, after the designation "Assignee," the name "Kunstoff-Spritzgusswerk" should read:

"Kunststoff-Spritzgusswerk"

Signed and Sealed this

Eighteenth Day of June 1985

[SEAL]

Attest:

DONALD J. QUIGG

Attesting Officer     Acting Commissioner of Patents and Trademarks